(12) United States Patent
Menard et al.

(10) Patent No.: US 10,478,158 B2
(45) Date of Patent: Nov. 19, 2019

(54) PEROPERATIVE SENSING HEAD ADAPTED TO BE COUPLED TO AN ABLATION TOOL

(75) Inventors: Laurent Menard, Palaiseau (FR); Sébastien Bonzom, Cachan (FR); Yves Charon, Bures sur Yvette (FR); Marie-Alix Duval, Les Ulis (FR); Françoise Lefebvre, Palaiseau (FR); Stéphane Palfi, Le Val Saint Germain (FR); Laurent Pinot, Lardy (FR); Rainer Siebert, Villepreux (FR); Stéphanie Pitre, Nanterre (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 2039 days.

(21) Appl. No.: 11/992,020

(22) PCT Filed: Sep. 12, 2006

(86) PCT No.: PCT/EP2006/066287
§ 371 (c)(1),
(2), (4) Date: May 12, 2009

(87) PCT Pub. No.: WO2007/031522
PCT Pub. Date: Mar. 22, 2007

(65) Prior Publication Data
US 2010/0063523 A1    Mar. 11, 2010

(30) Foreign Application Priority Data

Sep. 13, 2005 (FR) ...................................... 05 09329

(51) Int. Cl.
*A61B 1/00* (2006.01)
*A61B 10/02* (2006.01)
(Continued)

(52) U.S. Cl.
CPC ............ *A61B 10/02* (2013.01); *A61B 5/0084* (2013.01); *A61B 5/4836* (2013.01); *A61B 90/36* (2016.02); *A61B 90/39* (2016.02); *A61B 17/22004* (2013.01); *A61B 2017/00477* (2013.01); *A61B 2090/392* (2016.02); *A61B 2090/3908* (2016.02); *A61B 2090/3937* (2016.02); *A61B 2090/3941* (2016.02); *A61B 2562/0233* (2013.01)

(58) Field of Classification Search
CPC .................................................... A61B 6/425
USPC ........ 600/104, 112, 117, 129, 181, 182, 114, 600/128, 476, 478; 250/366, 367, 370.06, 250/370.08, 370.09
See application file for complete search history.

(56) References Cited

U.S. PATENT DOCUMENTS

4,870,950 A     10/1989  Kanbara et al.
5,008,546 A *    4/1991  Mazziotta et al. ............ 250/366
(Continued)

*Primary Examiner* — Timothy J Neal
(74) *Attorney, Agent, or Firm* — Osha Liang LLP (57) ABSTRACT

The invention concerns a preoperative probe (2) for guiding an ablation tool, comprising a sensing head (21), said sensing head including: at least one optic fiber (2121, 2123) for receiving and guiding a signal emitted, by radioactive tracers and/or fluorescent molecules in a tissue zone, to an analyzing equipment (32), fixing means (2112) for mounting the head (21) on the ablation tool (1), such that the ablation tool is capable of extracting a portion of tissue in the tissue zone emitting the signal.

30 Claims, 3 Drawing Sheets

(51) Int. Cl.
     *A61B 5/00*        (2006.01)
     *A61B 90/00*      (2016.01)
     *A61B 17/22*       (2006.01)
     *A61B 17/00*       (2006.01)

(56) References Cited

U.S. PATENT DOCUMENTS

| | | | |
|---|---|---|---|
| 5,014,708 A * | 5/1991 | Hayashi | G01T 1/161 600/105 |
| 5,088,492 A * | 2/1992 | Takayama | A61B 1/05 348/162 |
| 5,155,365 A * | 10/1992 | Cann et al. | 250/363.02 |
| 5,170,055 A * | 12/1992 | Carroll | A61B 6/4057 250/336.1 |
| 5,331,961 A * | 7/1994 | Inaba et al. | 600/436 |
| 5,377,683 A | 1/1995 | Barken | |
| 5,424,546 A * | 6/1995 | Okada | G01T 1/2008 250/367 |
| 5,600,144 A * | 2/1997 | Worstell | 250/363.03 |
| 5,651,783 A | 7/1997 | Reynard | |
| 5,719,400 A * | 2/1998 | Cherry et al. | 250/368 |
| 5,779,686 A * | 7/1998 | Sato | A61B 10/06 604/110 |
| 5,811,814 A * | 9/1998 | Leone | A61B 6/4258 250/368 |
| 6,149,593 A * | 11/2000 | Gonzalez-Lepera | A61B 6/00 250/303 |
| 6,456,869 B1 * | 9/2002 | Raylman | A61B 6/425 250/370.01 |
| 6,495,834 B1 * | 12/2002 | Corvo et al. | 250/363.1 |
| 6,643,538 B1 * | 11/2003 | Majewski | A61B 1/042 348/162 |
| 2002/0077643 A1 | 6/2002 | Rabiner et al. | |
| 2002/0168317 A1 * | 11/2002 | Daighighian et al. | 600/407 |
| 2003/0045780 A1 * | 3/2003 | Utsui | 600/104 |
| 2004/0116807 A1 * | 6/2004 | Amrami et al. | 600/476 |
| 2005/0043617 A1 * | 2/2005 | Frisch et al. | 600/478 |
| 2005/0181383 A1 * | 8/2005 | Su et al. | 435/6 |

* cited by examiner

PEROPERATIVE SENSING HEAD ADAPTED TO BE COUPLED TO AN ABLATION TOOL

The present patent application is a national phase application of International Application No. PCT/EP2006/066287, filed Sep. 12, 2006.

The invention relates to assistance with the surgical treatment of biological tissue, in particular of cancerous tumours.

Assistance with the surgical treatment of cancer is currently based on several techniques.

In a first type of technique called "pre-operative imaging techniques", before the operation the surgeon creates an image of the tissue area to be treated in order to locate, as well as possible, the tissue parts to be excised.

Pre-location of the tumour, by means of x-ray tomography or of IRM is used, for example, to obtain the precise anatomical topography of the tumorous volume and thus to choose the most appropriate surgical approaches. When coupled with mechanical stereotaxic or optical guidance, preoperative location leads to more narrowly defined and therefore less traumatizing access paths, especially in the case of deep lesions.

In neurosurgery, this technique can be complemented by the use of a functional isothermal remanent magnetization (IRM) imaging appliance, which is used, before the surgical procedure, to precisely identify the functional cerebral zoned located close to the tumour. On the basis this information, the surgeon is then able to optimize the extent of the zone to be excised while also minimizing the risks of postoperative morbidity.

Preoperative imaging techniques have allowed the introduction of surgical procedures that are more precise and less invasive.

However, these techniques have limits in terms of performance and ergonomic design. In particular, these techniques are ill-suited to operations requiring location of small tumours and their metastatic disseminations if any.

In addition, the displacement of the tissue during the surgical procedure (in particular in the brain) often renders obsolete the location of lesions effected before the operation.

According to a second type of technique, the surgeon takes tissue samples during the operation, and these samples are analyzed extemporaneously, so as to ensure the quality of the operating procedure of the surgeon.

These techniques, which rely upon precise anatomopathological diagnosis of the tissue samples have the advantage of being very reliable.

Such techniques are very costly however.

In addition, the time necessary to obtain a diagnosis from the samples may sometimes significantly increase the time of the surgical procedure.

Given the drawbacks associated with the preoperative imaging techniques and the tissue sampling techniques, a third type of technique called "preoperative techniques" has appeared. These techniques employ monitoring tools that are suitable of working in an operating suite, and thus of supplementing the outside imagers by helping the practitioner to determine the margins of a tumorous resection or a biopsy more precisely and in real time.

Two families of preoperative technique are currently under study. The first family of techniques, called "anatomical preoperative techniques", is based upon standard anatomical imaging systems, such as optical endoscopy systems, ultrasound echography, x-ray tomography or isothermal remanent magnetization (IRM). The second family of techniques, called "functional preoperative techniques", are based upon the detection of signals emitted by the tissue by virtue of miniaturized systems. The signals are particles or radiation emitted by radioactive tracers or fluorescent molecules present in the tissue and specific to the tumorous lesions looked for.

According to the anatomical preoperative techniques, in order to guide his actions, the surgeon uses an anatomical imaging appliance identical in principle to those used in clinical diagnosis departments but whose characteristics, in terms of dimensions and ergonomy, have been adapted for use in operating suites.

As a complement to preoperative examination, low-field IRM and the x-ray tomography are used mainly in the operating suite in order to correct location errors associated with the displacement of the tissue during the procedure and to guide the biopsy procedures. The anatomical imaging systems are in fact used to repeat, in real time, the images created before the procedure and, as a consequence, to monitor the distortion of anatomical structures in real time. Evaluation of the preoperative IRM for surgery of the gliomas has thus shown that these techniques allow one to improve identification of the extent of the tumorous resection in relation to the procedures in which only stereotaxic guidance based on preoperative images was used.

Ultrasound echography is also used in the operating suite to assist with the surgical treatment of tumours. This technique has the advantage of being a lot less expensive and costly to put in place than low-field IRM or x-ray tomography. The principal field of application of preoperative ultrasound echography is the location of non-palpable breast tumours and tumours of the liver. More generally, this technique is particularly adapted for the precise location of deep lesions.

According to the functional preoperative techniques, the surgeon uses a miniaturized detection device that is suitable for detecting radioactive tracers or light radiation specific to the histology or the physiological or metabolic behaviour of the tumorous lesions looked for. Since the function of an organ is often disrupted before its structure, these techniques are therefore theoretically more sensitive and specific than anatomical preoperative techniques in order to distinguish the healthy tissue from the cancerous tissue.

It is thus possible to optimize identification of the extent of the tumorous resection beyond the margins identified by the preoperative examination and without having to wait for the results of extemporaneous examinations of tissue samples.

These techniques can also be used to improve the diagnosis precision of biopsies by guiding the surgeon to relevant regions of tissue to determine the histological nature of the tumour.

In general, miniaturization of the detection devices used also leads to easier application of the functional preoperative technique in the operating suite, since it only slightly modifies the surgical protocol in relation to the more expensive and restrictive anatomical preoperative techniques.

Various counting or functional preoperative imaging devices have been developed. Some are even currently commercialized. However these devices are notable for several instrumental and methodological limits. Since there currently exists no system for functional preoperative imaging that allows the location and the simultaneous excision of the tumorous tissue. The current protocols combine two different tools which are used sequentially—the detection system (probe, microscope) and the excision tool (ultrasound aspiration device or electric lancet). This dissociation leads to correlation errors between the position of the tumour identified on the image and its actual position in the wound, and therefore reduces the precision of the excision procedure, in particular in the absence of anatomical location. The other limit of the functional preoperative devices relates their specific natures (associated with the tracers used) that is not total and therefore results in a non-negligible number of false negatives.

One aim of the invention is to allow the surgeon to perform an ablation with better precision and greater rapidity than with the devices of the prior art.

This problem is solved in the context of the present invention by using a preoperative probe to guide an excision tool in accordance with claim 1.

The detection head is adapted to be coupled to an excision tool so that the surgeon can perform detection and tumorous ablation operations in a single procedure, and with a single instrument.

More precise location of the tumorous tissue is thus achieved, because the correlation errors between the position of the tumour obtained from the signal the probe and its actual position in the operative wound are eliminated.

The ability to simultaneously measure the concentration of radioactive tracers and fluorescent molecules also allows one to benefit from the complementarity of the information acquired by these two methods, and therefore to reinforce the specificity of tumour detection.

Advantageously, a probe according to the invention measuring a signal emitted by fluorescent molecules in a tissue area, in response to a light excitation signal, also measures a light signal obtained by reflection of the light excitation signal by the tissue. The specificity is still further increased.

By virtue of the detection head, which records the signals emitted by the tissue, the surgeon can observe the treated tissue area in real time.

Advantageously, it is possible to couple the probe to a neuronavigation system so as to allow the surgeon to view the position of the probe in relation to the tumour and to the various cerebral structures identified during the preoperative IRM.

In addition, the detection head can easily be replaced by a detection head with different characteristics, in order to adapt the probe to the specific constraints of the different surgical protocols, as well as to the different signals emitted by the tissue.

The probe is particularly suitable for the surgical excision of tumours of the central nervous system, including the brain and the spinal marrow. In fact, more than for any other cancer, the precision of the surgical treatment of this pathology determines the vital and functional prognosis of the patient.

The probe can exhibit the characteristics of claims 2 to 10.

The invention also relates to a transmission and analysis tool for a preoperative probe according to the foregoing definition, with the tool being in accordance with claim 11.

The tool can exhibit the characteristics of claims 12 to 25.

Finally, the invention relates to a set for the surgical treatment of biological tissue according to claim 26.

Other characteristics and advantages or the invention will emerge from the description that follows, which is purely illustrative and non-limiting and should be read with reference to the appended figures, in which:

FIG. 1 schematically represents a set for the surgical treatment of biological tissue according to one embodiment of the invention, FIG. 2 schematically represents, in a front view, a detection head of a preoperative probe according to one embodiment of the invention, FIG. 3 schematically represents, in a side view and in section, a detection head of a preoperative probe according to one embodiment of the invention, FIG. 4 schematically represents, in a side view and in section, a detection head of a preoperative probe according to a variant of the embodiment of FIG. 3, FIGS. 5A and 5B schematically represent, in a side view and in section, connection components intended to allow connection between optical fibres of the detection head of the probe and optical fibres for transmission to analysis resources.

Figure 1:
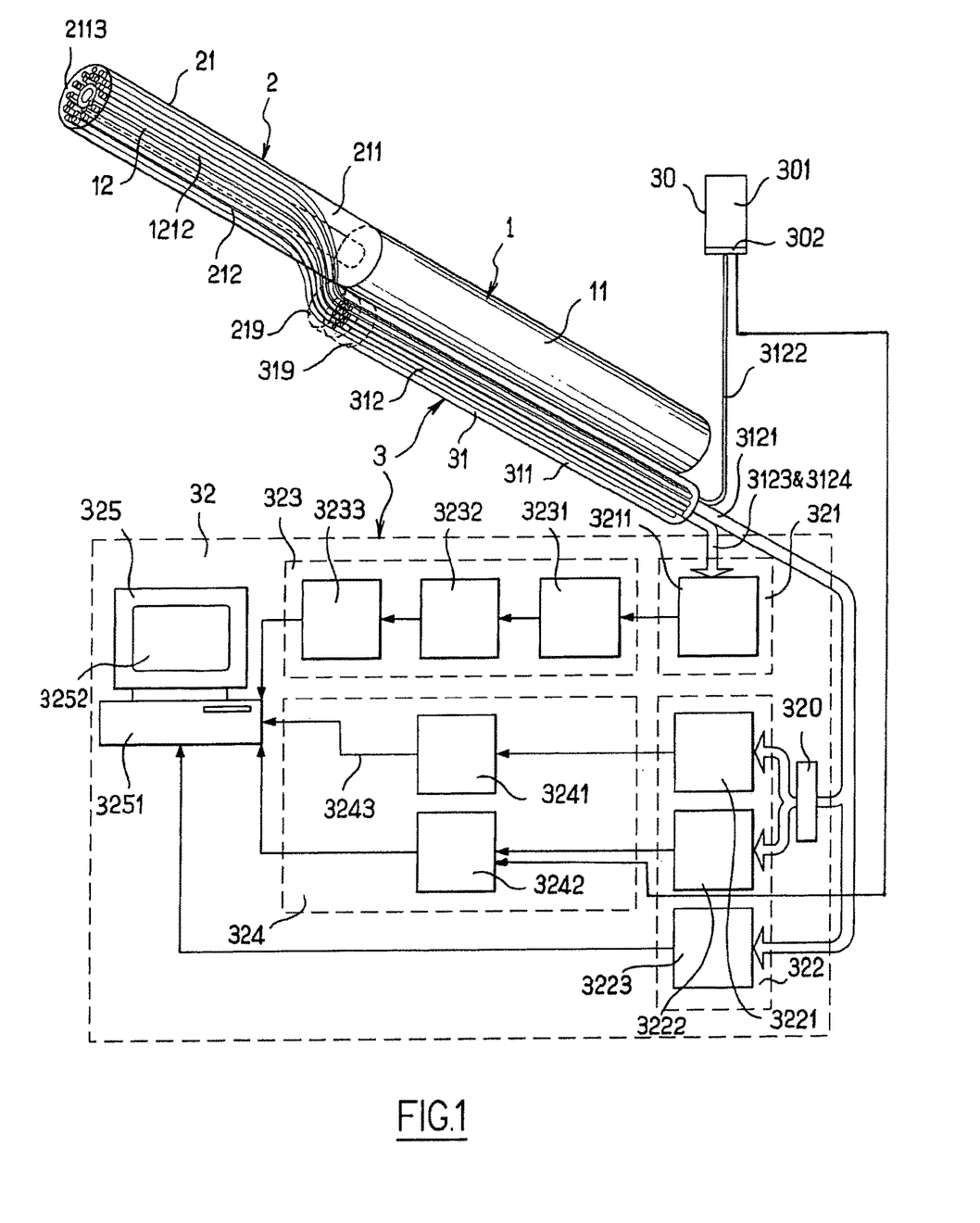

In FIG. 1, the set for the surgical treatment of biological tissue represented includes an excision tool 1, a preoperative probe 2, and means of transmission and analysis 3.

The excision tool 1 includes a gripping part 11 and an excision part 12. The excision tool 1 is an ultrasound aspiration device for example, in particular used during the surgical treatment of gliomas in order to excise the tumorous tissue. In the case of an ultrasound aspiration device, the excision part 12 includes a tube 1212 for the emission of ultrasound and for the aspiration of pulverized tissue.

The preoperative probe 2 includes a detection head 21 forming a part for clinical use. The detection head takes the form of an end-section adapted to be fitted tightly onto the excision tool 1.

The detection head 21 includes a body 211 of generally cylindrical shape, a bundle 212 of detection optical fibres extending inside the body 211 and a connection component 219.

The transmission and analysis means 3 include a light source 30, a reusable transmission element 31 and an analysis instrument 32.

The light source 30 includes a laser or a lamp 301 and an excitation filter 302. The laser or the lamp 301 is adapted to emit light in the form of a continuous ray or light pulses of controlled length. The filter 302 is adapted to filter the light generated by the laser or the lamp 301 and to transmit an excitation signal containing photons with wavelengths adapted to excite fluorescent molecules contained in the tissue to be treated. The fluorescent molecules then emit a fluorescent light signal, whose wavelength is different from the wavelength of the excitation signal. The fluorescence is in fact electromagnetic radiation, usually in the form of visible or infrared light, coming from the emitting fluorescent molecules excited by a light excitation signal of shorter wavelength. The fluorescent radiation ceases suddenly when the excitation stops.

The transmission element 31 includes a body 311, a bundle 312 of transmission optical fibres extending inside the body 311 and a connection component 319. Connection component 319 is adapted to mate with connection component 219 in order to connect each detection optical fibre of the detection head 21 bundle 212 to a transmission optical fibre of the transmission element 31 bundle 312.

Figure 2:
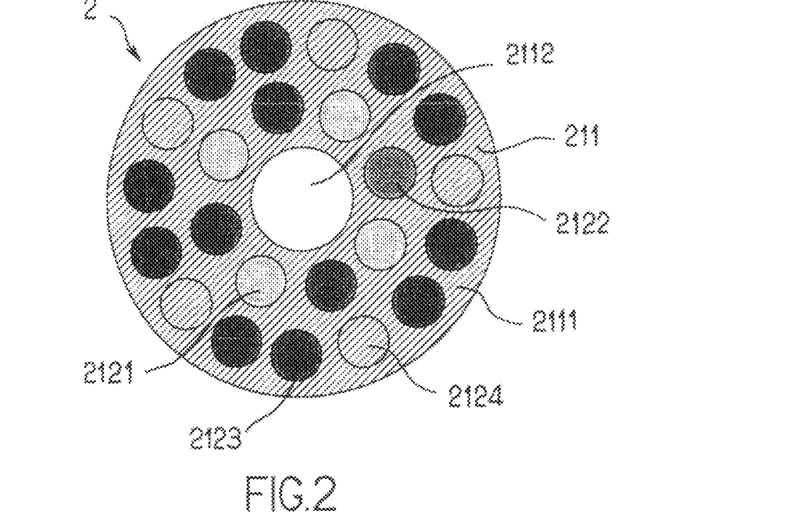
Figure 3:
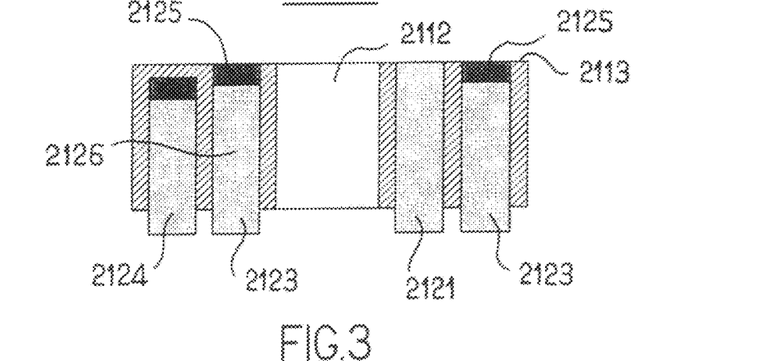

As illustrated in FIGS. 1 to 3, the detection head 21 includes a body 211 and a bundle 212 of detection optical fibres lying inside the body 211, in the longitudinal direction of the latter.

The body 211 is generally of tubular shape. The body 211 includes a cylindrical wall 2111 formed in metal, in stainless steel for example, or in any other material that is compatible with a surgical procedure, and a central channel 2112. The wall 2111 encloses the bundle 212 of detection optical fibres. The optical fibres of the bundle 212 are distributed around the central channel 2112 and lie substantially parallel to the central channel 2112.

The bundle 212 of optical fibres includes a plurality of fibres 2121 for detecting light radiation, one excitation fibre 2122, a plurality of radioactive tracer detection fibres 2123, and a plurality of control fibres 2124.

The fibres 2121, 2122 and 2123 lie between an end surface 2113 of the body 211 and the connection component 219. More precisely, the ends of the fibres 2121, 2122 and 2123 are flush with the surface 2113.

The fibres 2121 for detecting light radiation are composed of clear fibres. These fibres 2121 are adapted to receive and guide a light signal emitted by biological tissue.

The excitation fibre 2122 is also composed of a clear fibre. This fibre 2122 is adapted to guide a light excitation signal generated by the source 30 in the direction of the biological tissue, so as to excite fluorescent molecules contained in this tissue.

The radioactive tracers detection fibres 2123 include a scintillating end portion 2125 and a main clear portion 2126, with the scintillating end portion 2125 being fused to the main clear portion 2126, by heating for example. The scintillating end portion 2125 is adapted to interact with radioactive β particles ($\beta^+$ particles or $\beta^-$ particles) emitted by the tissue previously marked by radioactive tracers and to convert them into a light signal. The main portion 2126 is adapted to guide the light signal emitted by the end portion 2125.

The scintillating portion 2125 typically has a length of about 1 mm and the clear portion 2126 typically has a length of about 10 cm. The scintillating 2125 and clear 2126 portions typically have a diameter of the order of 1.5 mm.

The control fibres 2124 are identical to the radioactive tracer detection fibres 2123, except that the control fibres 2124 are rendered blind to the β particles. More precisely, the control fibres 2124 lie below the end surface 2113 of the body 211, so that the end of the control fibres 2124 is obstructed by a metal layer with a thickness of about 400 μm.

The radioactive tracers detection fibres 2123 and the control fibres 2124 are sensitive to γ radiation of 511 electron volts (eV) emitted by the tissue after the annihilation of $\beta^+$ particles. This γ radiation represents background noise in the detection of $\beta^+$ particles. The control fibres 2124 allow one to quantify the γ radiation with a view to subtracting it from the signals measured by the fibres 2123 and to thus to obtain a signal due to the $\beta^+$ particles only.

To allow more precise quantification of the γ radiation, the plastic scintillator may be replaced by an inorganic scintillator such as Lutetium Oxyorthosilicate doped with cerium (LSO) for example, which has a higher density and therefore a better detection efficiency for the γ radiation.

The wall 2111 in which the optical fibres 2121, 2122, 2123 and 2124 of the detection bundle 212 are buried constitutes a screen for the fibres. This screen isolates the fibres from the ambient light and any parasitic β particles that could arrive at the scintillating portions 2125 from the sides or via the rear of the fibres 2123.

Figure 4:
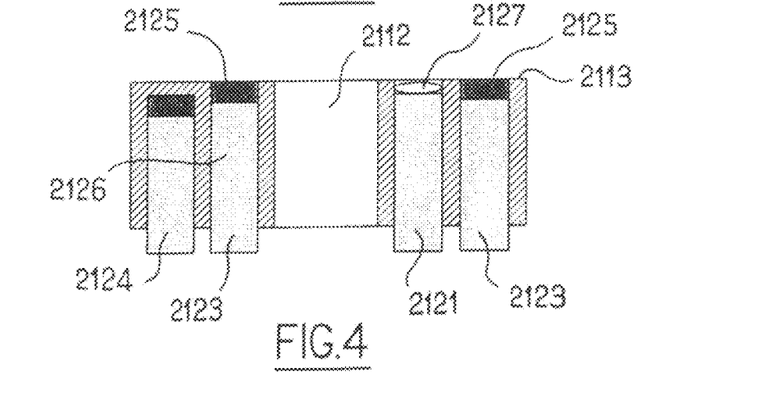

FIG. 4 illustrates a variant of the detection head 21. In this variant, the fibres 2121 and 2122 of the detection head does not extend to the end surface 2113 of the body 211. More precisely, the fibres 2121 and 2122 lie below the surface 2113. The detection head includes an optical element 2127 associated with each fibre 2121 and 2122, which focuses the light coming from the tissue to the fibres 2121 and which focuses the light coming from the fibre 2122 to the tissue. Each optical element 2127 includes a microlens for example. Focusing of the incident light allows to increase the local light concentration and, as a consequence, the sensitivity of the treatment set. In addition, the collection of the light coming from the tissue with the aid of a microlens improves the spatial resolution of the treatment set.

Figure 5A:
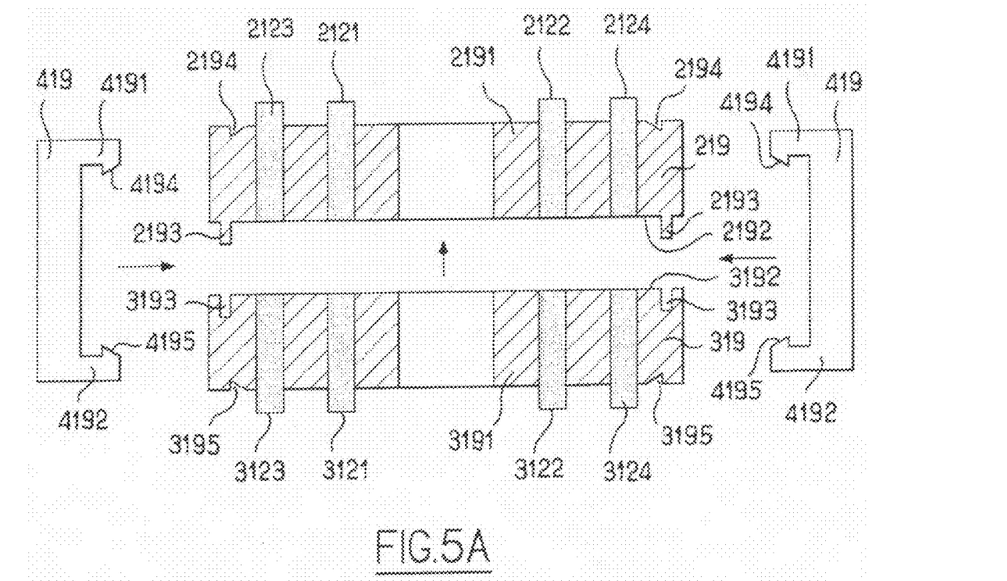
Figure 5B:
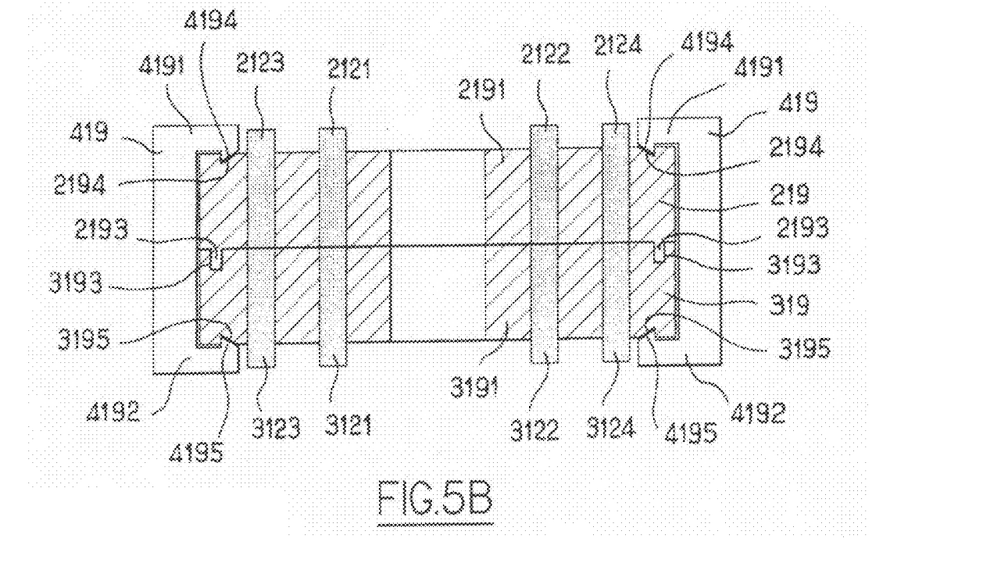

FIGS. 5A and 5B schematically represent an example of connection components 219 and 319 intended to allow connection between the detection optical fibre bundle 212 of the detection head 21 and the transmission optical fibre bundle 312 of the transmission element 31.

In FIG. 5A, the connection components 219 and 319 are detached from each other.

Connection component 219 includes a body 2191 in which detection fibres 2121, 2122, 2123 and 2124 are buried. The body 2191 includes a plane connection surface 2192. The ends of the fibres 2121, 2122, 2123 and 2124 are flush with the connection surface 2192.

Likewise, connection component 319 includes a body 3191 in which transmission fibres 3121, 3122, 3123 and 3124 are buried. The body 3191 includes a plane connection surface 3192. The ends of the fibres 3121, 3122, 3123 and 3124 are flush with the connection surface 3192.

Body 2191 includes connection studs 2193 projecting from the connection surface 2192. Body 3191 includes connection orifices 3193 extending back from the connection surface 3192. The studs 2193 are adapted to be inserted into the orifices 3193 in order to orientate the connection components 219 and 319. In addition, the studs 2193 and the orifices 3193 are arranged so that when the studs 2193 are inserted into the orifices 3193, connection surface 2192 comes into contact with connection surface 3192, and the ends of fibres 2121, 2122, 2123 and 2124 come into contact respectively with the ends of fibres 3121, 3122, 3123 and 3124, in order to connect the fibres together.

The surgical treatment set can also include locking components 419 intended to hold the connection components 219 and 319 in engagement. Each locking components is U-shaped and includes two branches 4191 and 4192. At each free end, each branch 4191 and 4192 respectively has a projection 4194 and 4195.

Each of the connection components 219 and 319 respectively includes notches 2194 and 3195.

The locking components 419 are adapted to hug together the connection components 219 and 319 when they are in mutual engagement. To this end, the components 219 and 319 are inserted between the branches 4191 and 4192 of the locking components 419. The presence of the projections 4194 and 4195 causes the separation of the branches 4191 and 4192 by elastic deformation. The projections 4194 and 4195 are then adapted to be inserted into the notches 2194 and 3195 by elastic return of the branches 4191 and 4192.

In FIG. 5B, the connection components 219 and 319 are brought into mutual engagement and the locking components 419 hold the connection components 219 and 319 in mutual engagement.

As can be seen in FIG. 1, the single-use detection head 21 is adapted to be attached in a detachable manner to the excision tool 1. To this end, the excision part 12 of the tool 1 is adapted to be inserted into the detection head 21. More precisely, the aspiration tool 1212 of the excision tool 1 is adapted to be inserted into the channel 2112 of the detection head 21 so that the aspirating end of the aspiration tool 1212 is flush with the end surface 2113 of the detection head 21.

Secondly, the connection components 219 and 319 are adapted to be brought into mutual engagement in order to couple the bundle 212 of detection optical fibres optically to the bundle 312 of transmission optical fibres. The connection components 219 and 319 are detachable connection components, which allows easy manual connection and disconnection.

The single-use detection head 21 can therefore be replaced easily by another head.

The transmission element 31 typically has a length of 2 metres, to route the light signals coming from the detection head 21 to the analysis equipment 32 located outside the operative field.

When the connection components 219 and 319 are brought into engagement, the light radiation detection fibres 2121, the excitation fibre 2122, the radioactive tracers detection fibres 2123, and the control fibres 2124, of the detection head 21 bundle 212 are respectively connected to transmission fibres 3121, 3122, 3123 and 3124 of the transmission element 21 bundle 312.

The transmission fibres 3121 are connected to the clear fibres 2121 of the detection head 21 and are adapted to guide light radiation coming from the tissue.

The transmission fibre 3122 is connected firstly to the source 30 and secondly to the excitation fibre 2122 so as to guide the excitation radiation, emitted by the source 30, to the tissue to be treated.

Fibres 3123 and 3124 are adapted to guide the light signals generated by the interaction between the β particles and the γ radiation emitted by the tissue with the scintillating portions 2125 of the fibres 2123 and 2124.

The analysis equipment 32 includes a first photodetection unit 321, a second photodetection unit 322, a first acquisition unit 323, a second acquisition unit 324 and a PC 325.

Fibres 3123 and 3124 of bundle 312 are connected to the first photodetection unit 321.

The first photodetection unit 321 includes a multianode photomultiplier 3211. The multianode photomultiplier 3211 includes a plurality of pixels (typically 64 pixels), each pixel or group of pixels being coupled to a fibre 3123 or 3124 of the bundle 312. Each pixel of the multianode photomultiplier is adapted to convert a light signal that it receives into an electrical signal.

The first acquisition unit 323 includes a resistance network 3231, pre-amplification electronics 3232 and amplification electronics 3233.

The resistance network 3231 is adapted, according to the principle of the load division, to supply a position of the baric centre and an intensity of the light signal coming from the fibres 3123 and 3124. These data are used to determine the number of fibres affected and the quantity of energy given up by a β particle or the γ radiation to the scintillating portions 2125 of the fibres 2123 and 2124.

The pre-amplification electronics 3232 and the amplification electronics 3233 are adapted to integrate and then to amplify the signals generated by the resistance network 3231. The unit 323 then transmits the analogue to the PC 325 for their digitization and their treatment.

In addition, the fibres 3121 of the bundle 312 are connected to the second photodetection unit 322.

The second photodetection unit 322 includes a fibre spectrophotometer 3221, an ultra-rapid detector 3222, such as a detector supplied by the Hamamatsu Photonics company under the reference R3805U MCP PMT, and an avalanche photodiode or a multianode photomultiplier 3223 including built-in analysis electronics, such as a photodiode supplied by the Id QUANTIQUE company under the reference id100-20. The fibre spectrophotometer 3221 is adapted to detect the intensity of a light signal that it receives in a plurality of wavelengths making up the light signal, and to convert the intensity into an electrical signal. The ultra-rapid detector 3222 is adapted to measure the arrival time of a light signal that it receives, and to convert the arrival time into an electrical signal. The avalanche photodiode or the multianode photomultiplier 3223 is adapted to convert a light signal that it receives into a standard electrical signal.

The second acquisition unit 324 includes a first conversion electronics unit 3241 and a second routing electronics unit 3242.

The first conversion electronics unit 3241 is adapted to convert the analogue signals generated by the fibre spectrophotometer 3221 into digital signals, in order to allow direct transfer to the PC 325 via a USB cable 3243.

The second routing electronics unit 3242 is adapted to connect, in parallel, several signals generated by one or more ultra-high-speed detectors 3222 to a photon counting card, also measuring their time of passage.

The PC 325 includes a digitizing and calculating unit 3251 and a display screen 3252. The digitizing and calculating unit 3251 is adapted to receive and to process the signals generated by units 323 and 324. The digitizing and calculating unit 3251 is also adapted to control the display screen 3252.

The use and the operation of the surgical treatment set that has just been presented will now are described.

Before an operation, the surgeon chooses a detection head 21 that is suitable for the operative wound and for the type of tumour to be treated.

The surgeon attaches the detection head 21 to the excision tool 1 by inserting the aspiration tool 1212 into the channel 2112 of the detection head 21.

Then the surgeon connects the fibre bundles 212, 312 together by means of the connection components 219 and 319.

During the operation, the surgeon performs the excision of a visible part of the tumour.

Next, the surgeon inserts the end of the probe 2 into the operative wound. More precisely, the surgeon positions the probe 2 so that the end surface 2113 of the detection head 21 is positioned facing a tissue zone to be treated. The surgeon moves over the operative wound by means of the detection head 21 and positions the detection head 21 in a plurality of successive positions. For each position of the head 21, the surgeon creates a mapping of the signals emitted from the tissue zone facing the end surface 2113. For each position of the detection head 21, the acquisition time of the mapping does not exceed a few seconds.

The preoperative probe allows firstly to detect particle-emitting radioactive tumorous tracers.

When a β particle emitted by the tissue area is received by one of the fibres 2123, the scintillating portion 2125 of the fibre 2123 generates a light signal (a pulse) that is guided by the clear portion 2126 of the detection fibre 2123.

The light signal is guided to the photodetection unit 321 by a transmission fibre 3123 of the transmission element 31. The light signal is received by a pixel of the photomultiplier 3211 that generated an electrical signal (electrical pulse) that is proportional to the intensity of the light signal.

The electrical signal is processed by the acquisition unit 323 that supplies, by means of the resistance network 3231, a number associated with the fibre 2123 affected by the β particle, and energy is given up to the scintillating portion 2125. The acquisition unit 323 amplifies and digitizes the signals generated by the photodetection unit 321, and transmits the amplified signals to the digitizing and calculating unit 3251.

In addition, the transmission fibres 3124 guide the light signal obtained from the control fibres 2124 that are sensitive only to the γ radiation generated by the tissue.

The γ radiation resulting from annihilation of the β+ particles in the tissue, represents background noise for the process of locating tumorous lesions in the operative wound. These signals can in fact come from regions, specific or non specific to attachment of the β+ tracer, that are very distant from the tissue zone analyzed by the probe.

In order to distinguish the γ signals from the β+ signals, the surgical treatment set has the following characteristics.

According to a first characteristic, the scintillating portions 2125 of the fibres 2123 are formed from a plastic material, which are not very sensitive to the high-energy γ radiation. In fact the plastic material has a low density (typically 1.05 g/cm3 and is composed of elements with a low atomic number (6 at most for Carbon). The simulated γ efficiency of a scintillating plastic fibre, 2 mm in diameter and 1 mm in length, located to 0.1 mm from a one-off source of $^{18}$F, is thus about 300 impacts per second per microCurie (cps/µCi) against a β+ efficiency of $1.7.10^4$ cps/µCi in the same configuration.

In the case of treatment of a cerebral tumour, this radiation can come from the whole of the brain however. The contribution of the γ background noise to the β+ signal can therefore become very high, despite the intrinsic low sensitivity of the plastic material constituting the scintillating portion.

According to a second characteristic, the digitizing and calculating unit 3251 is adapted to select the signals that it receives according to the energy of the particle that has interacted with the scintillating portion. The theoretical study of the energy spectrum of the γ radiation that has interacted with the scintillating portion in fact shows that 40% of the γ detected radiation generates an energy of between 0 and 1000 keV, while the energy distribution of the β+ particles is between 0 and 500 keV.

The digitizing and calculating unit 3251 is therefore adapted to select only the signals whose energy is greater than a threshold of between 50 and 100 kiloelectronvolt (keV).

According to a third characteristic, each radioactive tracer detection fibre 2123 is associated with a control fibre 2124. The control fibres 2124 are sensitive to the γ radiation but are insensitive to the β+ particles. The unit 3251 is adapted to subtract, from the count corresponding to the signals generated by a radioactive tracer detection fibre 2123, the γ count corresponding to the signals generated by the associated control fibre 2124, in order to obtain a measurement of the β+ signal only.

It will be noted in this regard that several radioactive tracer detection fibres 2123 can be associated with a single control fibre 2124 so as to optimize the portion of the detection surface 2113 sensitive to the β particles.

The digitizing and calculating unit 3251 is adapted to compare the count of the pulses corresponding to the radioactive tracer concentration measures at the fibres 2123 of the detection head 21 with a reference count measured previously in a zone of the operative wound composed of healthy tissue only.

When the difference between the measured count and the reference count is greater than a threshold standard deviation (greater than 3 for example), then the unit 3251 will identify the tissue area as tumorous.

The digitizing and calculating unit 3251 commands the screen 3252 so that the latter displays a mapping of the tissue area on which the number of β particles detected by each fibre 2123 is indicated.

The surgeon may thus view an image of the treated tissue zone on the screen 3252 in real time, which indicates the distribution of the radioactive tracer concentration at the fibres 2123 of the detection head 21.

The preoperative probe is also used for tumorous tissue detection by fluorescent optical techniques.

Thus, the clear fibres 2121 receive the fluorescent radiation emitted by fluorescent molecules present in the tissue after the molecules have been excited by a light excitation signal conducted by the fibre 2122 to the tissue. The light signal containing the fluorescent light radiation is guided by the clear fibres 2121. The light signal is then guide via the transmission fibres 3121 of the bundle 312 to the photodetection unit 322. For the analysis of the fluorescent signal, the light signal is processed by a filter 320 that cuts off the wavelengths of the excitation radiation in order to select only the fluorescent radiation.

The fluorescent light signal is received firstly by the fibre spectrophotometer 3221 and secondly by the ultra-high-speed detector 3222. The fluorescent radiation may also be filtered and then received by the avalanche photodiode or the photomultiplier 3223. The three devices 3221, 3222 and 3223 each generates an electrical signal.

The fibre spectrophotometer 3221 determines a spectrum of the fluorescent radiation and generates an electrical signal that is used for counting the radiation, a measurement of the wavelength of the radiation, and a number identifying the fibre that has guided the radiation.

The avalanche photodiode or the multianode photomultiplier 3223 generates an electrical signal that is adapted to effect the counting of the fluorescent radiation.

The ultra-high-speed detector 3222 generates an electrical signal corresponding to the time of passage of the fluorescence photons and a number identifying the fibre that has guided this photon. These signals are used to measure the decay time of the fluorescence radiation in relation to the moment of tissue excitation (meaning at the moment of emission of a pulse from the light source 30).

The acquisition unit 324 digitizes the signals generated by the spectrophotometer 3221 and transmits the digitized signals to the digitizing and calculating unit 3251. The unit 3242 also effects a routing of the signals generated by the ultra-high-speed detector or detectors 3222 and transmits the signals to the specific digitization card of the digitizing and calculating unit 3251. The signals generated by the detector 3223 are transferred directly to the counting card of the unit 3251.

The digitizing and calculating unit 3251 is adapted to compare the count of the radiation detected by the fibres 2121 with a reference count, measured previously in a zone of the operative wound composed of healthy tissue only. When the difference between these counts is greater than a predetermined threshold (the count has a standard deviation greater than 3 in relation to the reference count for example), the unit 3251 will identify the tissue area as tumorous.

In addition, the digitizing and calculating unit 3251 is adapted to compare a spectrum of the fluorescent radiation detected by the fibres 2121 with a reference spectrum measured previously in a zone of the operative wound composed of healthy tissue only. The comparison is created for one or more ranges of wavelength of the measured spectrum. For example, when the "red" contribution of the spectrum (wavelengths between 600 and 700 nm) is greater by more than 100% in relation to the reference spectrum, the unit 3251 will identify the tissue area as tumorous.

In addition, the digitizing and calculating unit 3251 is adapted to calculate the decay time of the florescence from the signals of the unit 3242 and to compare these with reference times measured previously in a zone of the operative wound composed of healthy tissue only. When at least one of the measured decay times has a standard deviation that is greater by 50% in relation to the reference time, the unit 3251 will identify the tissue area as tumorous.

Finally, the digitizing and calculating unit 3251 is adapted to process in combination the various data produced by the devices 3233, 3241, 3242 and 3223. The identification of tumorous tissue is thus based on complementary data and leads to results that are more reliable than with independent use of the different data.

In particular, for several measurements based on different independent parameters from the same tissue area indicating a tumorous zone without however exceeding the thresholds specified for a reference zone, the unit 3251 will identify the zone as tumorous. In the opposite case, in which a meaningful measurement (standard deviation greater than 3) is not confirmed, or if it is contradicted by other measurements, then the unit 3251 will not propose excision of the corresponding tissue.

The processing unit 3251 controls the screen 3252 so that the latter displays several two-dimensional graphs each representing the tissue area. The first graph indicates the count of the β tracers at each fibre 2123.

The unit 3251 may command the screen 3252 to present a second graph representing the intensity of the fluorescent radiation according to the wavelength of the radiation. Beforehand, the surgeon will have chosen a wavelength window and, in this second graph, the screen 3251 will display only the intensity of the fluorescent radiation at the fibres 2121 whose wavelengths are between the lower limit and the upper limit of the window chosen by the surgeon.

The unit 3251 also controls the screen 3252 so that the screen 3252 displays a third graph representing the decay time of the radiation emitted by the fluorescent molecules detected at the fibres 2121.

The surgeon may thus view several mappings of spatial distributions of measured intensities and of the parameters specific to the treated tissue zone on the screen 3252, in real time.

The screen 3252 may simultaneously display several measured mappings and superimposed these on each other.

The screen 3252 may also display a table summarizing the results of the measurements taken individually and offer conclusions to the surgeon. According to the mapping or mappings displayed by the screen 3252, the surgeon may decide whether to excise the tissue zone by means of the excision tool 1.

It will be noted that the number and arrangement of the optical fibres in the detection head 21 can easily be modified, so as to meet the constraints of the different surgical protocols.

The probe 2 may be rendered more versatile by providing a range of interchangeable detection heads 21 that satisfy the various specifications (compactness, sensitivity, resolution, etc.).

It is thus possible to provide a detection head that included only on clear fibre 2121 and one excitation fibre 2112 for detection of the fluorescent molecules present in the tissue.

It is also possible to provide a detection head that includes only one radioactive β tracer detection fibre 2123 and one control fibre 2124. This type of detection dead is particularly suitable for surgical procedures that require extreme compactness of the probe, such as excision procedures under endoscopy or biopsies.

At the other extreme, it is possible to provide a detection head that includes several concentric layers of detection fibres 2121 and 2123, used to perform mapping of the spatial distribution of the radioactive tracers and of the light radiation in a field of view of the order of 2 square centimetres ($cm^2$). This type of detection head is suitable for surgical procedures that call for rapid exploration of the operative wound, or for operations that are limited by high non-specific fixing of the radioactive tracers.

In contrast to a counting probe, the option to create a mapping of the tissue area to be treated in fact allows one to distinguish the tumorous signals specific to the background noise, and therefore to improve the signal to noise ratio, which can be badly affected by the heterogeneity of the tracer fixing in the tissue surrounding the lesion.

Between these two extreme configurations just presented, detection heads with intermediate arrangements of fibres, in terms of number and positioning, may also be envisaged.

Advantageously, it is possible to combine and sum the data coming from each fibre in a single signal. The sum is then used as a single mono-pixel detector, in such a way that the probe has a better sensitivity for more rapid identification of the zones to be treated.

The treatment set just described allows simultaneous measurement of the concentration of radioactive tracers and the fluorescent molecule distribution. This association is used to increase the complementarity of the histological, metabolic and molecular data supplied by these different measurements, and thus to increase the efficiency of preoperative detection of tumours.

The probe just described is of small dimensions and is easy to manipulate, thus allowing access to narrow regions of operative wounds (cavities of the order of 3 to 5 cm for cerebral tumours for example).

In addition, the probe allows precise and rapid location of the zones of tissue to be excised.

Coupling with the excision tool in fact allows the surgeon to view, in real time, a mapping of the tissue area located close to the excision tool, and therefore to perform a more precise and rapid excision of the tumorous tissue in a single procedure, having first marked it out.

Finally, the probe allows more specific detection of the tumours than with the techniques of the prior art. In fact, combining the detection of several types of tracer allows one to supply more precise and reliable information on the nature of the tissue treated.

A probe according to the invention, measuring a signal emitted by fluorescent molecules in a tissue area, in response to a light excitation signal, advantageously also measures a light signal obtained from the reflection of the light excitation signal by the tissue.

In the foregoing developments, a bundle of micro-optical fibres of very small diameter can naturally replace each optical fibre described.

The invention claimed is:
1. A system for performing neurosurgery comprising:
a handheld device comprising an excision tool and a probe, the handheld device configured to be manipulated by a neurosurgeon to detect and excise tumorous tissue of a patient's central nervous system, the probe configured to generate a first output corresponding to detection of beta particles and gamma radiation emitted by radioactive tracers absorbed by the tumorous tissue and a second output corresponding to detection of gamma radiation alone;

a processing system having a monitor, the processing system configured to be coupled to the handheld device to receive and process the output of the probe and compare the first output to the second output to determine a concentration of beta particles emitted by the radioactive tracers, the processing system generating and displaying on the monitor, in real time, an image corresponding to the concentration of beta particles emitted by the radioactive tracers in the tumorous tissue that identifies a margin of the tumorous tissue, the image enabling the neurosurgeon to manipulate the handheld device to excise, and observe treatment of, tumorous tissue in real time.

2. The system of claim 1, wherein the probe comprises:

a detection head comprising a tubular member defining an end face, a side wall, an interior space, a plurality of holes extending through the end face and communicating with the interior space, and a tool opening extending through the end face and communicating with the interior space to permit passage of a distal end of the excision;

an array of optical fibers, each optical fiber having a proximal end and a distal end, wherein the distal end of each optical fiber is disposed in the interior space of the detection head;

a first scintillating portion coupled to the distal end of each optical fiber of a first subset of the array of optical fibers, each first scintillating portion disposed adjacent to one of the plurality of holes extending through the end face, each first scintillating portion configured to interact with beta particles, emitted by the radioactive tracers, that pass through a corresponding hole in the end face and with gamma radiation to generate the first output;

a second scintillating portion coupled to the distal end of each optical fiber of a second subset of the array of optical fibers, each second scintillating portion disposed within the detection head below the end face to shield each optical fiber of the second subset of the array of optical fibers from the beta radioactive particles emitted by the radioactive tracers, each second scintillating portion configured to interact with gamma radiation to generate the second output, each optical fiber of the second subset of the array of optical fibers being paired with one or more of the optical fibers of the first subset of the array of optical fibers; and a photodetector comprising a plurality of pixels, each pixel operatively coupled to a corresponding one of the optical fibers in the array of optical fibers to receive the first output or the second output, the photodetector generating an output comprising pixel-by-pixel values, wherein the image generated by the processing system corresponds to differences between pixel values for pixels receiving the first output and pixel values for pixels receiving the second output.

3. A system according to claim 2, wherein the detection head includes at least one clear optical fiber adapted to receive a fluorescent light signal emitted by fluorescent molecules in the tumorous tissue.

4. A system according to claim 3, wherein the detection head also includes a lens to focus the signal emitted by the fluorescent molecules on the clear optical fiber.

5. A system according to claim 2, wherein the detection head also includes at least one clear optical fiber adapted to route an excitation signal to the tissue so that the fluorescent molecules in the tissue emit a fluorescent signal.

6. A system according to claim 5, wherein the probe further comprises a light excitation source adapted to be connected to a proximal end of the at least one clear optical fiber.

7. A system according to claim 6, wherein the light excitation source includes a filter adapted to select a specific excitation wavelength or range of excitation wavelengths.

8. A system according to claim 5, further comprising a spectrophotometer adapted to measure an intensity of a fluorescent signal emitted by the tumorous tissue.

9. A system according to claim 5, wherein the probe further comprises a detector adapted to measure an arrival time in relation to an excitation signal emitted to the tumorous tissue.

10. A system according to claim 5, wherein the probe further comprises a filter adapted for filtering a part of the light signal resulting from light excitation radiation reflected by the tumorous tissue, and for transmitting a part of the light signal resulting from fluorescent radiation emitted by the tumorous tissue.

11. A system according to claim 2, wherein the plurality of holes extending through the end face of the detection head are distributed around the tool opening.

12. A system according to claim 2, wherein the detection head includes a connector to route signals emitted by the detection head to the photodetector.

13. A system according to claim 2, wherein the detection head is for one-time use only.

14. A system according to claim 2, wherein the tool opening is disposed within the end face at a central location surrounded by the plurality of holes.

15. A system according to claim 2, wherein the excision tool comprises an ultrasonic ablation tool and aspiration lumen.

16. A system according to claim 2, wherein the image is a two dimensional image.

17. A system according to claim 2, wherein the photodetector comprises a multianode photomultiplier.

18. A system according to claim 2, wherein the photodetector comprises an avalanche photodiode.

19. The system of claim 1 wherein the probe comprises:

a detection head comprising a tubular member defining an end face, a side wall, an interior space, a plurality of holes extending through the end face and communicating with the interior space, and a tool opening extending through the end face and communicating with the interior space to permit passage of a distal end of the excision tool;

an array of optical fibers, each optical fiber having a proximal end and a distal end, wherein the distal end of each optical fiber is disposed in the interior space of the detection head;

a first scintillating portion coupled to the distal end of each optical fiber of a first subset of the array of optical fibers, each first scintillating portion disposed adjacent to one of the plurality of holes extending through the end face, each first scintillating portion configured to interact with beta particles, emitted by the radioactive tracers, that pass through a corresponding hole in the end face and with gamma radiation to generate the first output;

a second scintillating portion coupled to the distal end of each optical fiber of a second subset of the array of optical fibers, each second scintillating portion disposed within the detection head below the end face to shield each optical fiber of the second subset of the array of optical fibers from the beta radioactive particles emitted by the radioactive tracers, each second scintillating portion configured to interact with gamma radiation to generate the second output, each optical fiber of the second subset of the array of optical fibers being paired with a one or more of the optical fibers of the first subset of the array of optical fibers; and a photodetector comprising a plurality of pixels, each pixel operatively coupled to a corresponding one of the optical fibers in the array of optical fibers to receive the first output or the second output, the photodetector generating an output comprising pixel-by-pixel values, wherein the processing system is configured to generate a two-dimensional image corresponding to intensities of the beta particles received by the first subset of optical fibers and differences between pixel values for pixels receiving the first output and pixel values for pixels receiving the second output.

20. A system according to claim 19, wherein the detection head includes at least one clear optical fiber adapted to receive a fluorescent light signal emitted by fluorescent molecules in the tumorous tissue.

21. A system according to claim 20, wherein the detection head also includes a lens to focus the signal emitted by the fluorescent molecules on the clear optical fiber.

22. A system according to claim 21, including a light excitation source adapted to be connected to a proximal end of the at least one clear optical fiber.

23. A system according to claim 22, wherein the light excitation source includes a filter adapted to select a specific excitation wavelength or range of excitation wavelengths.

24. A system according to claim 21, further comprising a spectrophotometer adapted to measure an intensity of a fluorescent signal emitted by the tumorous tissue and further comprising a detector adapted to measure an arrival time in relation to an excitation signal emitted to the tissue.

25. A system according to claim 19, wherein the probe further includes at least one clear optical fiber adapted to route an excitation signal to the tumorous tissue so that fluorescent molecules in the tissue emit a fluorescent signal.

26. A system according to claim 19, wherein the plurality of holes extending through the end face of the detection head are distributed around the tool opening.

27. A system according to claim 19, wherein the detection head includes a connector to route signals emitted by the detection head to the photodetector.

28. A system according to claim 19, wherein the detection head is for one-time use only.

29. A system according to claim 19, wherein the tool opening is disposed within the end face at a central location surrounded by the plurality of holes.

30. A system according to claim 19, wherein the excision tool comprises an ultrasonic ablation tool and aspiration lumen.

* * * * *